United States Patent [19]

Takahashi et al.

[11] 3,942,897
[45] Mar. 9, 1976

[54] METHOD AND APPARATUS FOR DETECTING SOLID SUBSTANCES CONTAINED IN LIQUID

[75] Inventors: Toshio Takahashi, Honjo; Ryosaku Tagaya, Isezaka; Toshiyasu Ehara, Misato, all of Japan

[73] Assignee: Eisai Co., Ltd., Tokyo, Japan

[22] Filed: Oct. 29, 1974

[21] Appl. No.: 518,940

Related U.S. Application Data

[62] Division of Ser. No. 409,368, Oct. 25, 1973.

[30] Foreign Application Priority Data

Oct. 31, 1972 Japan............................. 47-108524
May 24, 1973 Japan............................. 48-59379

[52] U.S. Cl................................. 356/197; 356/104
[51] Int. Cl.²........................................ G01N 15/02
[58] Field of Search........... 356/104, 197; 350/96 B; 209/73, 111.7

[56] References Cited
UNITED STATES PATENTS

| | | |
|---|---|---|
| 2,635,194 | 4/1953 | Kellogg et al................... 356/197 X |
| 3,415,997 | 12/1968 | Vinzelberg et al............. 356/197 X |
| 3,591,290 | 7/1971 | Zinner et al...................... 356/102 |
| 3,602,640 | 8/1971 | Maillet et al.................. 350/96 B X |
| 3,811,567 | 5/1974 | Tomita et al. .................. 356/197 X |

Primary Examiner—Alfred E. Smith
Assistant Examiner—Wm. H. Punter
Attorney, Agent, or Firm—Wenderoth, Lind & Ponack

[57] ABSTRACT

Method and apparatus for detecting and measuring solid alien substance(s), which may adversely exist in a liquid contained in a transparent container, are provided. Light is applied to the container as it is rapidly rotated and then suddenly stopped to cause floating or suspending the solid substance(s) in the liquid. The light passed through the liquid or passed through light and also the light reflected from the solid substance(s) are separately captured and their individual intensities are measured by means of photometry. The method and apparatus may be utilized for sorting out the transparent liquid from that contaminated with solid impurity, depending upon the intensity(s) of the captured light or lights.

3 Claims, 5 Drawing Figures

METHOD AND APPARATUS FOR DETECTING SOLID SUBSTANCES CONTAINED IN LIQUID

This application is a division of application Ser. No. 409,368 filed Oct. 25, 1973.

This invention relates to a novel method and apparatus for detecting and measuring solid alien substance(s) that may exist in admixture in a liquid contained in a transparent container.

For checking and selecting out the solid substances that may exist in admixture, for example, in medical liquids, liquid foods, liquid chemicals, chemical reagents, etc. contained in ampoules, bottles or other kinds of containers, there are known and used, besides the macroscopic inspection method, various types of effective and automatic liquid inspecting methods and apparatus utilizing a photoelectric element.

According to these known automatic inspection methods, light is projected onto a liquid container such as, for example, an ampoule and the scattered light rays that are reflected from the alien substances in the liquid are received by the photoelectric element. In this case, if no alien substance exists, the photoelectric element receives only the scattered light reflected from the liquid alone in the container such as an ampoule, whereas if any alien substance is present, said element receives the scattered light rays reflected from both the liquid and alien substance so that the amount of light received by the photoelectric element is increased. Therefore, it is possible to photoelectrically determine the quantity of the alien substance present in the liquid through comparative measurement of the amounts of light received.

However, the intensity or quantity of scattered light reflected from the alien substance mingled in the liquid is not only proportional to the reflection area of the alien substance, but is also greatly affected by the shape of the substance or its light reflectibility. For example, a black colored material generally has a smaller reflectibility than a white material. Accordingly, if the quantity of light reflected from a small-sized white material and that from a large sized black material are measured separately, there would be a case where it is erroneously judged that these two materials are the same size or are present in the same quantity. The essential function of the inspecting apparatus is to detect the alien substances having the sizes in excess of a certain preset standard value and to remove such oversized substances. Therefore, if an inspection standard is set on the basis of reflectability which is not always proportional to the size of the substance, the result of the measurements may prove incorrect and lead to erroneous results.

Now we have found, as one of the aspects of this invention, that accuracy of measurement can be remarkably improved by using a method in which, instead of measuring the intensity of light reflected from the alien matters, as in the conventional methods, light rays that have passed through the liquid are received on a plurality of small light-receiving faces and the corresponding electric outputs from these respective light-receiving regions are scanned and made into a single output. This method is based on the fact that as each of the plurality of light-receiving faces is equal in area to the projected image of the smallest one of the alien substances that are to be checked, the light-receiving faces are perfectly shaded by the alien substances. There is thus produced an extremely large difference in the amount of light received on said light-receiving faces between the cases where alien substances exist in the liquid and where alien substances do not exist.

Thus, according to the above-mentioned aspect of this invention, there is proposed a method in which, instead of measuring the scattered light rays reflected from the alien matters, shading of the direct light rays by the alien matters is taken into account in making the inspection. The mechanism of the present invention is such that an output is given by the photoelectric element only when the size of the alien matter exceeds a certain preset level. According to this method, it has been found that inspection for alien matters in a liquid to be examined can be accomplished with far higher accuracy than that obtained with any of the conventional methods. If anything, however, it may be said that the result obtained by carrying out this method is more or less affected by light permeability of the alien matters. For instance, a white slender and elongated solid matter, such as a filament-like substance, has a pale projected image and hence has lower sensitivity than a black matter of the same shape and size.

Such shortcomings as aforementioned can, however, be overcome by the second aspect of this invention, wherein the above-mentioned method according to the first aspect of this invention is combined with a known method by which the existence of solid alien matters is determined by measuring the reflected light from said solid matters.

With reference to the accompanying drawings.

The method of this invention will be hereinafter described by way of an embodiment as applied to an ampoule filled with a liquid such as liquid medicine.

Figure 1:
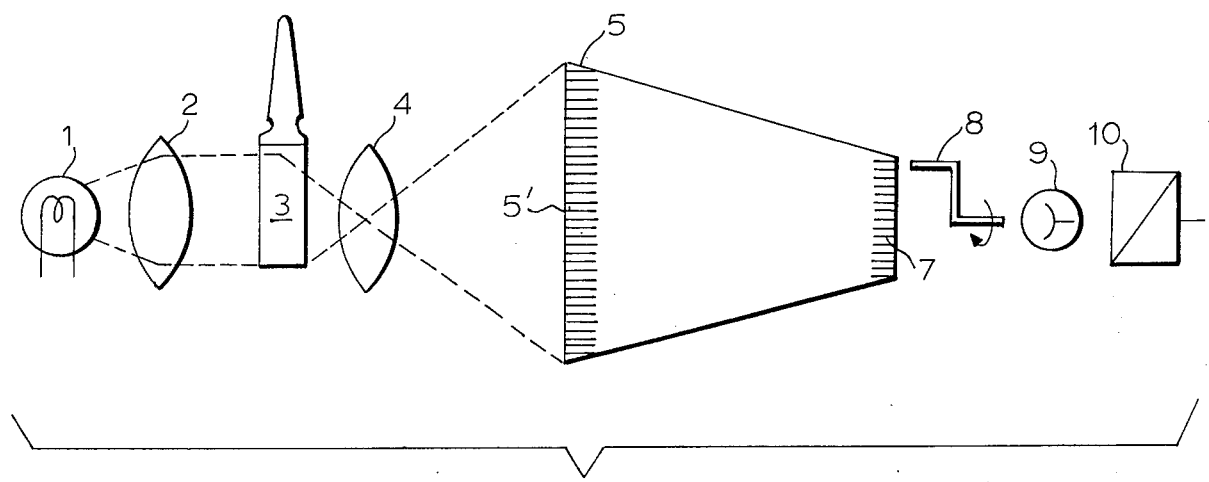
FIG. 1 is a diagrammatic view of an apparatus embodying the first aspect of the present invention.
Figure 2:
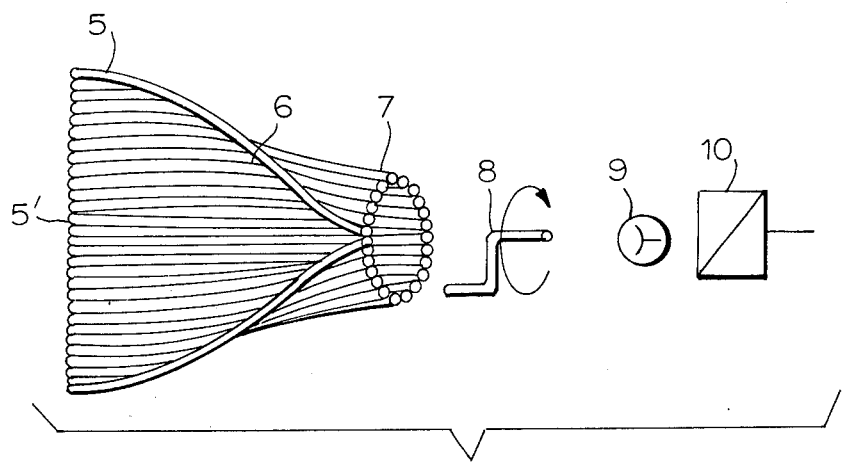
FIG. 2 is an enlarged view showing the construction of a known optical fiber system scanning device which can be used as the scanning unit constituting a part of the apparatus shown in FIG. 1.

In the first aspect of this invention, parallel light rays, as is later explained in more detail, with reference to accompanying FIGS. 1 and 2, are applied to an ampoule by directing light from a light source through a lens, the ampoule being secured to a revolvable support block where said ampoule will be rotated at a high speed and then stopped suddenly. Behind said ampoule is provided a focussing lens whereby the projected image of the ampoule is formed on a plane behind said lens. The light-receiving faces of a photoelectric converter provided with a scanning unit are provided on said plane. In case some solid alien substance exists in the liquid held in the ampoule, the direct light projected to the light-receiving faces from the light source is shaded by the solid alien substance so that the amount of light received by the shaded light-receiving faces is greatly decreased. This condition is converted into an electric signal by means of a scanning type photoelectric converting element. Thus, whether the ampoule contains any alien substance therein or not can be determined by the presence or absence of said signal.

In a preferable scanning unit, there is arranged on a straight vertical line a plurality of small light receiving faces, each of which has an area equivalent to at least the smallest regulated size of alien substances to be detected. Such light receiving faces may, for instance, be provided by a bundle of optical fibers used in an optical fiber type scanner, as shown in FIG. 2, or by a scanning type photo-diode array, and the mechanism is arranged such that these small light-receiving faces will be scanned one after the other successively.

As an example thereof, a rotary scanner using optical fibers is discussed with reference to FIG. 2 where such scanner is shown in an enlarged perspective view. This optical fiber type scanning unit consists of a plurality of optical fibers 6 each of which is as fine as $100\mu$ in size, a rotary scanning element 8, a photoelectric element 9 and an amplifier 10. Said plurality of optical fibers are arranged at one end in a straight vertical line to form a rectilinear end 5', while the other ends are arranged circularly to form a circular end 7 (straight line-circle converter system). The rotary scanning element 8 made of optical fiber is adapted such that its one end will rotatively scan along said circular end 7 of the optical fiber bundle 5, the other end of said scanning element 8 being optically connected to the light receiving faces of the photoelectric element 9. The light rays from a light source 1 are projected through an ampoule 3 (which has just been brought into a suddenly stopped condition from a high speed rotating condition) onto the light-receiving faces, each having a small section along the rectilinearly arranged end 5' of the optical fibers 6 and hence said light receiving faces are illuminated with a certain brightness. However, if any alien substance exists in the liquid in the ampoule, the projected image of such alien substance (which continues moving rotatively in suspension in the liquid, even after the rotation of the ampoule has been stopped suddenly) momentarily crosses said rectilinear end 5' so that the direct light rays from the light source to said light-receiving faces are shaded during such period of crossing to darken said faces. As such bright and shaded conditions at the linear end 5' are transmitted continuously to the circular end 7 through the optical fibers 6, the revolving scanning element 8 picks up such bright and shade conditions for every optical fiber at the circular end 7, and the picked up conditions are immediately converted into a strong or weak current by the photoelectric element 9 and the amplifier 10, and the measurement and selection of the inspected pieces are carried out by a suitable known method according to the electric signal produced by said conversion.

In the above-described embodiment of the present invention, the shading of light effected by the alien substance on the light receiving faces of the optical fibers is utilized in making the measurement, so that even in case the alien substance has a low reflectibility, there can be obtained a signal with high S-N ratio, ensuring a high degree of accuracy of measurement. Also, since the projected image with the same size as the diameter of one piece of optical fiber is equal to the minimum size of the alien substance detected, it is possible to optionally change the smallest size of the detectible alien substance by adjusting the magnification of the focussing lens.

As described above, if an ampoule is rotated at a high speed and then stopped suddenly, the liquid therein continues to move in a whirling motion by inertia, even after stoppage of the ampoule rotation, and hence the alien substance, if any, present in the liquid also continues to rotate in a floating condition together with the liquid. According to the present invention, light rays are projected on the solid alien substance in that condition.

A typical embodiment of the above will be illustrated in a more concrete manner with reference to FIG. 1.

Figure 4:
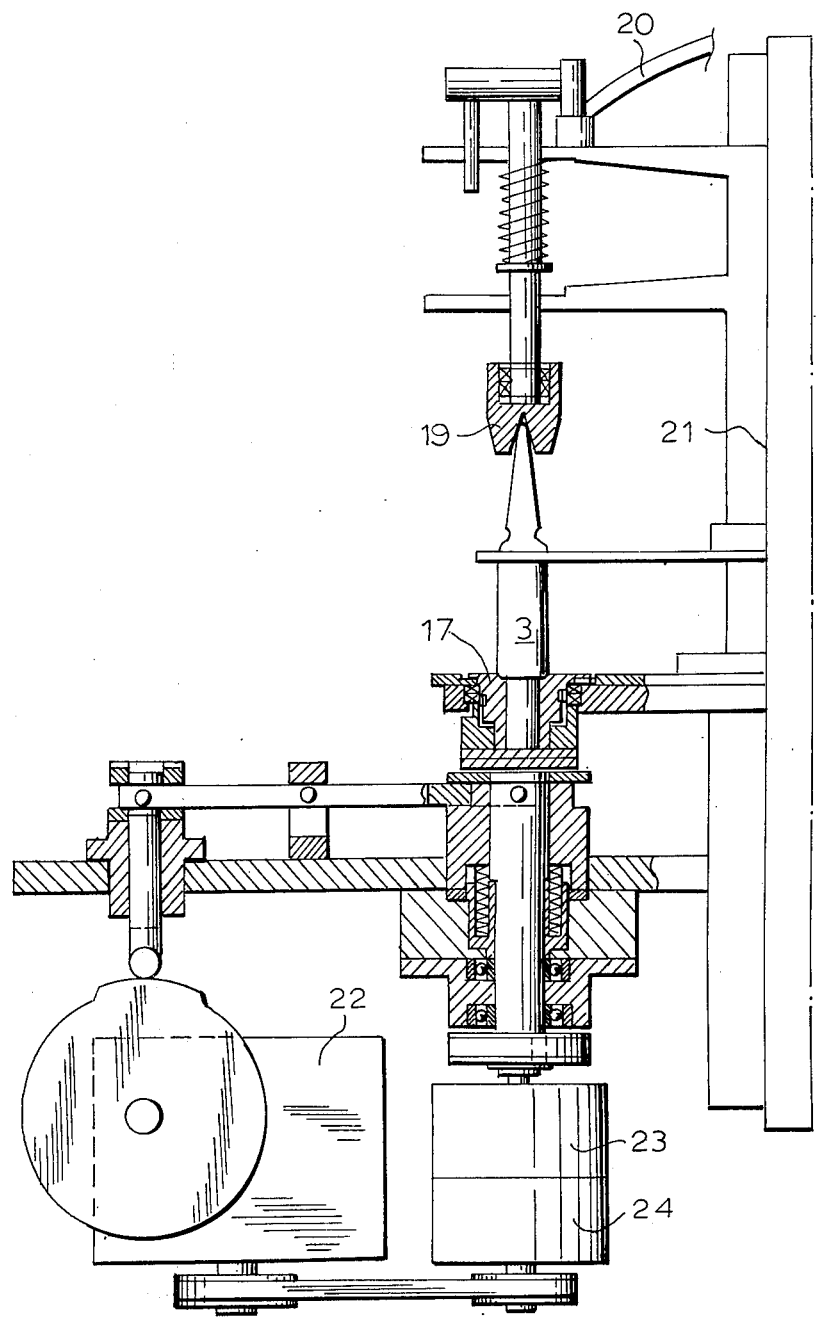
FIG. 4 shows a mechanism for supporting an ampoule filled with liquid, for example, for examination.

The illumination lamp 1 is lighted to form parallel light rays through a condensing lens 2 disposed in front of said lamp, and the light rays are passed through an ampoule 3 to be inspected which is fixed on a revolvable block or rest 17 as shown in FIG. 4. Said block is first rotated at a high speed and then stopped suddenly, whereby the alien solid substance present in the liquid of the ampoule is caused to move in a whirling motion in the ampoule together with the liquid. The projected image of this alien substance is formed on the rectilinear end 5' of the optical fibers 6 of the scanning unit by a focussing lens 4, whereby the direct light from the lamp 1 is shaded, that is, prevented from being projected onto the light-receiving faces of the optical fibers. The darkened state created by this shading of the projected light is communicated to the circular end 7 through the optical fibers 6, and the condition of the circular end 7 is picked up successively by the revolving scanning element 8 and transmitted to the light receiving faces to the photoelectric element 9 to be converted into an electric pulse signal, which is then further amplified with an amplifier 10 to produce an amplified signal. In this way, existance of alien substance, if any, is detected and converted into an electric pulse signal so that it is possible to know that solid impurities are present in the ampoule and to perform sorting out of the ampoule according to such electric signal.

The above-described optical fiber system scanning unit can be replaced by a known scanning type photo-diode array.

Figure 3:
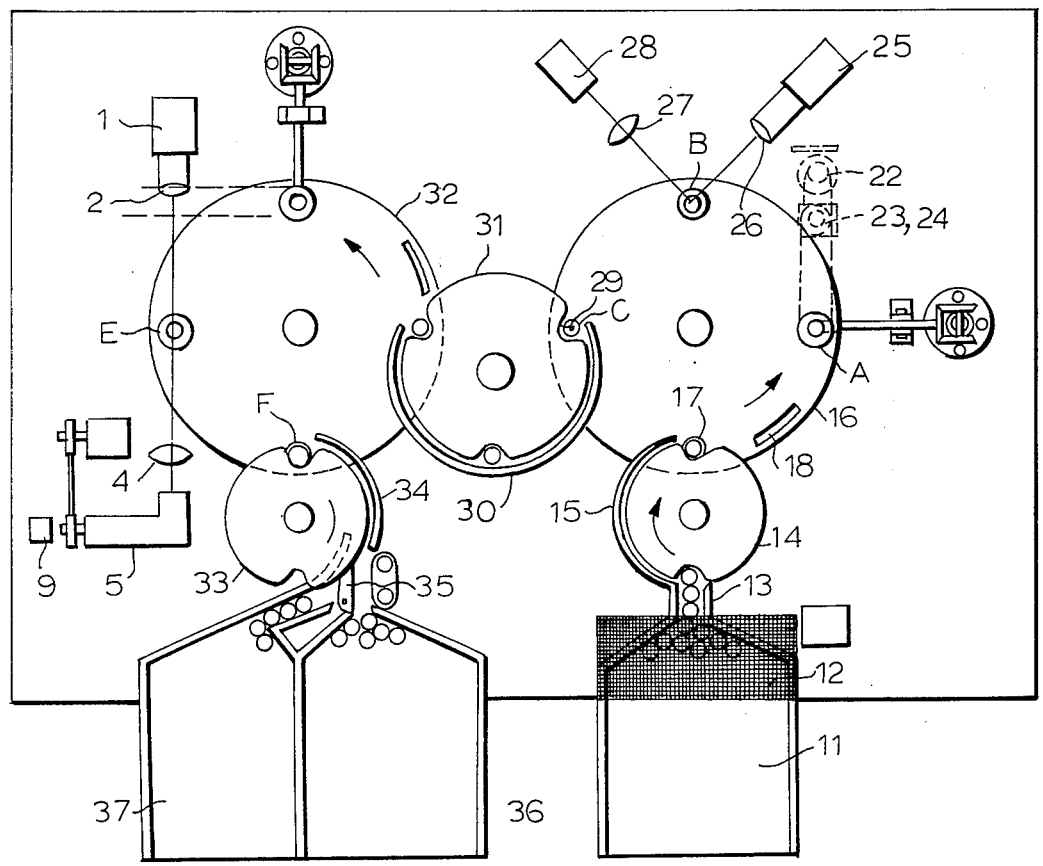
FIG. 3 is a plan view of the essential component parts in a preferred embodiment of the second aspect of this invention.

Turning to the second aspect of this invention, it should be emphasized that the result of the observation is not affected much at all by the shape or kind of the alien substances such as aforementioned, and that it is possible to detect with high accuracy the alien matters having areas or sizes greater than a certain preset standard. An embodiment thereof will be explained with reference to FIGS. 3, 4 and 5. Although there is shown in FIG. 3 an embodiment of the apparatus in which the reflected light is detected in the first step, and in the next step the transmitted light is separately captured, it is also possible to reverse the order of these two steps, and/or to provide an arrangement which will independently detect both the transmitted and reflected light with a single mechanism, or to provide plural reflected light capturing means and/or plural transmitted light capturing means for groups of a series of test pieces which are fed successively, so as to accomplish the same optical inspection over a plural number of test pieces at one and the same time. All of these modifications are within the scope of the present invention.

Referring to FIG. 3, the apparatus shown in plan view consists essentially of the following four sections:

a. a section where the ampoules (the objects to be examined) are successively supplied; (b) a section where the mechanism for examining the ampoule content with reflected light is located; (c) a section where the mechanism for examining the ampoule content with transmitted light is positioned; and (d) a section where the examined ampoules are sorted out and retrieved.

The ampoule supply section (a) consists of an ampoule feeding hopper 11, a new conveyor 12, a hopper guide 13, a feeding star wheel 14, and a star wheel guide 15. The bottom of the feeding hopper 11 is slanted toward the center, having a conical shape so that the ampoules supplied into said feeding hopper 11 are guided down in a row through the hopper guide 13 due to their own weight and with the aid of the net conveyor 12 spread at the end of the cone-shaped bottom portion of the hopper.

The ampoules thus fed in a row are then carried by the star wheel 14 one by one intermittently onto one of the revolveing ampoule rests 17 on a first turret 16 at an intermittent pitch of one-quarter turn of said turret 16. (In case four revolving ampoule rests 17 are provided on said turret, each piece, as shown in FIG. 4, is adapted to uprightly sustain an ampoule while rotating it therewith.)

Each of the four ampoules positioned vertically at the peripheral edge of the first turret 16 is retained at the center of each revolving ampoule rests by said star wheel and guide 15. As the turret turns, each said ampoule is held by a guide 18 and moved to the ampoule rotating means A.

During this movement, an upper cap 19 (see FIG. 4) descends to hold the ampoule with spring force so that the ampoule won't slip on its rest 17. The up and down movement of said upper cap 19 is effected through a cylindrical cam 20 which is secured by a fixed shaft 21 disposed at the center of the turret. The ampoule thus delivered to the ampoule rotating section A is rotated at high speed by the rest 17 and then suddenly stopped by the operation of a motor 22, brake 23 and clutch 24. Thereafter, by a turn of the turret, the ampoule is moved to the examining section B where the ampoule content is examined with reflected light.

Figure 5:
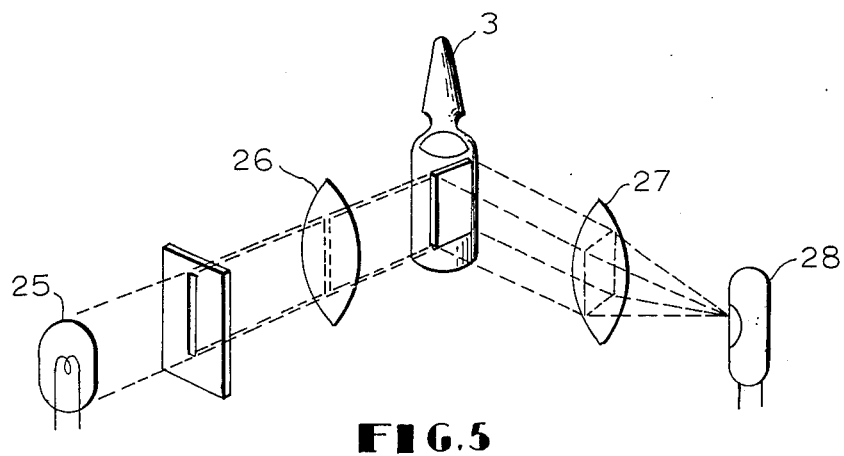
FIG. 5 is a diagram illustrating the known reflecting mechanism of the projected light, which may be used as the part of the arrangement for the embodiment of FIG. 3 according to the second aspect of this invention.

In this examining section B, as shown in FIG. 5, a slit-shaped light beam formed by a light source 25 and a lens 26 is projected to a side of the ampoule 3, and the scattered light reflected from the alien matters whirled up in the central portion of the ampoule liquid by the aforesaid high speed rotation and ensuing sudden stoppage is captured by means of a focussing lens 27 and a photoelectric element 28 (which may be a photomultiplier tube) which are disposed at a certain angle relative to the slit shaped beam, and the captured reflected light is immediately converted into an electric signal. This electric signal discriminates the good ampoules from the bad ones according to a preset pulse level, and the reject signals, if any, are memorized by a memory element.

The ampoule which has thus been examined in the examining section B is now moved to the discharge section C of the first turret 16. During this movement, the upper cap 19 ascends. Upon arriving at the discharge section C, the ampoule is pushed upwardly by a push-up rod which projects up through a hole provided in the center of the base of the support block 17. Then, the ampoule is caught and held by a guide 30 and discharged from the first turret 16 by the intermittent turning of a transfer star wheel 31 (turning at an intermittent one-third turn pitch), to deliver the ampoule to a second turret 32 where the content is further examined with the transmitted light. Thus, the ampoule is transferred by said star wheel 31 onto the second turret 32 in the same way as it was delivered to the first turret 16 and here again the ampoule is given a high speed rotating motion and guided to the examining section E of the second turret 32 where the ampoule is examined by transmitted light.

In this examining section E, the parallel light rays created by a light source 1 and a lens 2, as shown in FIG. 1, are projected through each ampoule so that its projected image will be formed on a plane behind a focussing lens 4 disposed behind the ampoule, said plane being of a known optical fiber assembly 5 having a scanning portion at the other end. The projected image screened by the alien matters whirled up in the central portion of the ampoule liquid is scanned by an optical fiber type scanner 8 and converted into an electric signal by a photoelectric element 9 and an amplifier 10 and further processed by an electronic mechanism, whereby the "good" and "bad" ampoules are discriminated according to a preset pulse level, with the reject signals being memorized by a memory element. After having been thus examined in the examing section E, the ampoule is then moved to the discharge section F of the second turret 32. In the discharge section F, the ampoule is discharged by means of a discharging star wheel 33 and a discharging star guide 34 in the same way as in the discharge section C of the first turret 16. The discharging star wheel 33 is provided with means 35 for sorting out the good ampoules and bad (non-conforming) ampoules. That is, the reject signals memorized in the examining section B and/or the reject signals memorized in the examining section E all indicate non-conforming ampoules, and the conforming ampoules are sorted out by means of a shutter operated by a rotary solenoid.

The thus sorted good ampoules are guided in order into a hopper 36 therefor, and the bad ampoules into a hopper 37 therefor for further processing.

As is well-known, all of the known automatic liquid inspecting methods necessitate to repeat the examination several times in order to increase accuracy and reliability of the inspection. However, no matter how many times the liquid inspecting method with a definite defect is repeated, it is impossible to overcome the inherent defective operating characteristics related to the kind and shape of the alien matter.

In contradistinction of the above, with the method of examining liquid according to the second aspect of this invention, wherein the reflected light and also the transmitted light are successively utilized in any order, it is possible to remove the defects inherent in these methods while making use of their advantageous effects. It thereby makes it possible to realize a method and an apparatus which are capable of detecting the solid alien matters in a liquid and sorting out from the conforming articles the non-conforming ones with an extremely high probability that has never been possible with any of the conventional methods.

What is claimed is:

1. A method for photometric determination of size and/or amount of solid matter that might be present as an impurity in a transparent liquid held in a sealed transparent vessel, comprising the steps of rapidly rotating the vessel around a vertical axis and then suddenly stopping the rotation to cause the solid matter to be suspended in the liquid; projecting light onto the vessel; and leading the scattered light reflected from the solid matter to a photometric device and measuring reflected light thereby; and leading the transmitted light through said vessel to a photometric scanning device provided with multiple optical elements, each having a minute light-receiving area, and successively measuring the light received by said multiple optical elements thereby.

2. An apparatus for the photometric determination of size and/or amount of solid matter that might be present as an impurity in a transparent liquid held in a sealed transparent vessel, comprising means for detachably securing the vessel; means for rapidly rotating the thus secured vessel around a vertical axis and then suddenly stopping said rotation; light source means for projecting light onto said vessel; a photometric means positioned adjacent said vessel for receiving and measuring the intensity of the scattered light reflected from any solid matter in the vessel; and a photometric scanning means provided having multiple optical elements positioned adjacent said vessel and in an array for receiving light from different parts of said vessel for measuring intensity of the light transmitted through said vessel.

3. An apparatus as claimed in claim 2 wherein said photometric scanning means has said multiple optical fibres arranged in a linear array along said vessel.

* * * * *